US00PP32926P2

(12) United States Plant Patent
Olesen

(10) Patent No.: US PP32,926 P2
(45) Date of Patent: Mar. 30, 2021

(54) HYBRID TEA ROSE PLANT NAMED 'POULREN030'

(50) Latin Name: *Rosa hybrida*
Varietal Denomination: Poulren030

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,992

(22) Filed: Sep. 3, 2020

(51) Int. Cl.
*A01H 6/74* (2018.01)
*A01H 5/02* (2018.01)

(52) U.S. Cl.
USPC ..... Plt./137

(58) Field of Classification Search
USPC ..... Plt./137
See application file for complete search history.

*Primary Examiner* — Annette H Para

(57) ABSTRACT

A new garden rose plant of the Hybrid Tea class which has abundant, pink flowers and attractive foliage. This new and distinct variety has shown to be uniform and stable in the resulting generations from asexual propagation.

3 Drawing Sheets

Botanical designation: *Rosa hybrida.*
Variety denomination: 'Poulren030'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulren030', originated as a single seedling from the stated cross.

The new variety may be distinguished from its male pollen parent and female seed parent primarily by the following characteristics. The male pollen parent plant grows to a height of 50 cm, while the new variety grows to a height of 80 to 120 cm. The female seed parent plant has apricot flowers while the new variety has pink flowers.

The objective of the hybridization of this rose variety was to create a new and distinct variety with unique qualities, such as:

1. Uniform and abundant pink flowers with strong perfume;
2. Vigorous, but compact growth when propagated on its own roots;
3. Exceptional disease resistance.

This combination of qualities is not present in previously available commercial cultivars of this type, known to the inventor, and distinguish 'Poulren030' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulren030' was selected in the spring of 2013 by the inventor as a single plant from the progeny of the aforementioned hybridization.

Asexual reproduction of 'Poulren030' by rooted cuttings was first done by Mogens N. Olesen in the nursery in Fredensborg, Denmark in July, 2013. This initial and other subsequent asexual propagations conducted in controlled environments have demonstrated that the characteristics of 'Poulren030' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren030'.

Specifically illustrated in FIG. 1 of the drawings are open flowers, flower petals and sepals detached, showing reproductive flower parts and receptacle.

Figure 1:
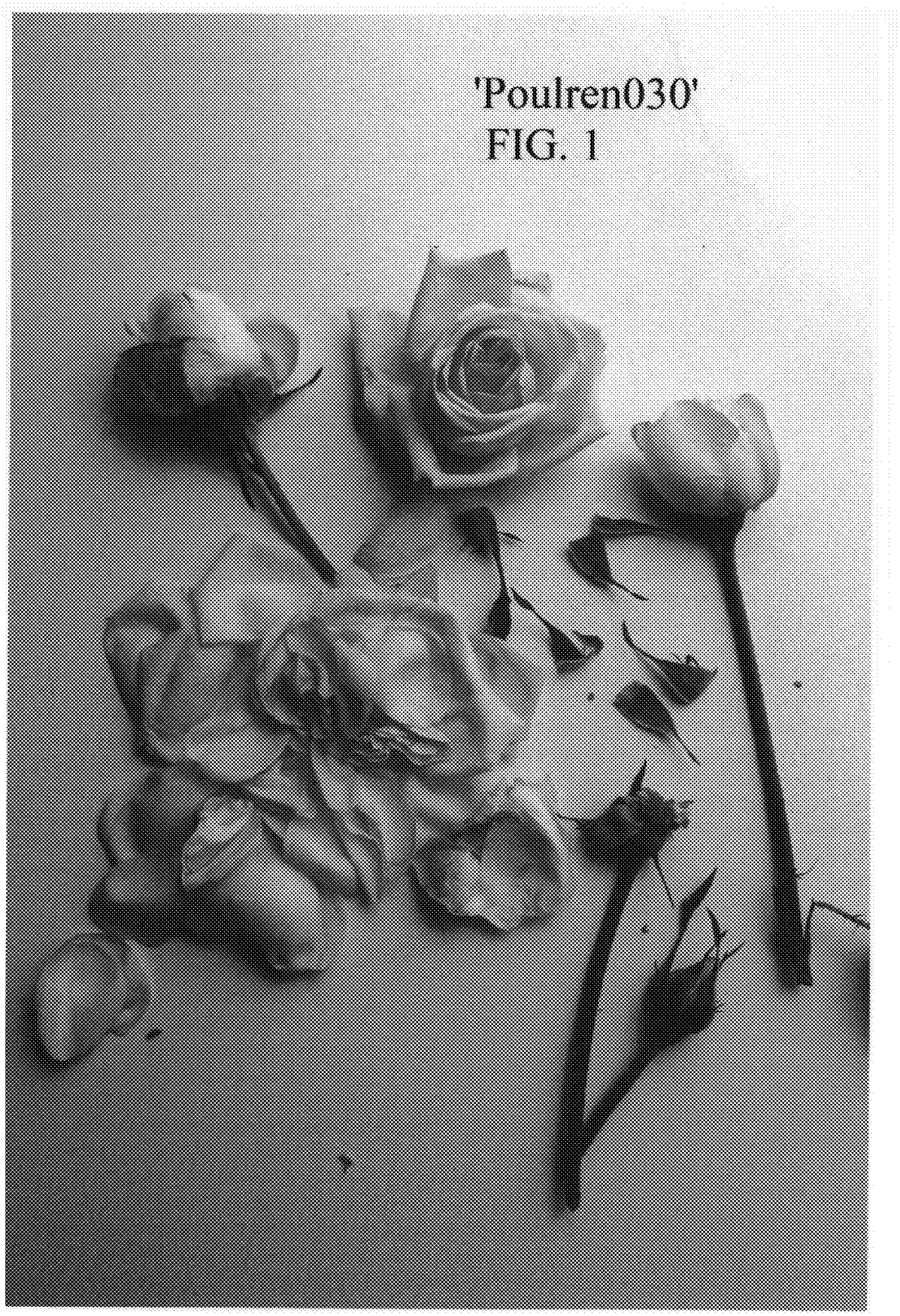
Figure 2:
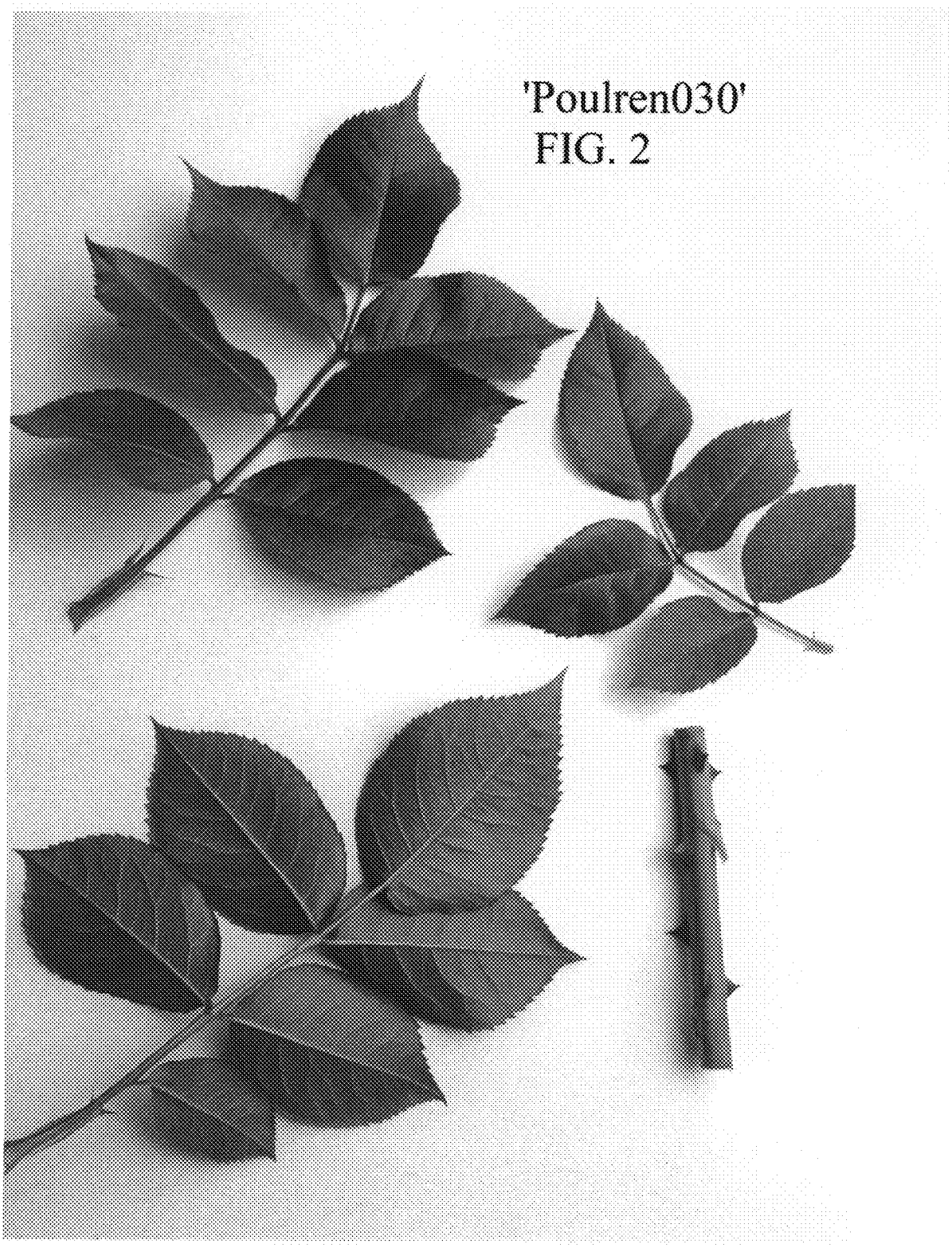

Specifically illustrated in FIG. 2 of the drawings are mature and juvenile leaves with bare stem exhibiting prickles.

Figure 3:
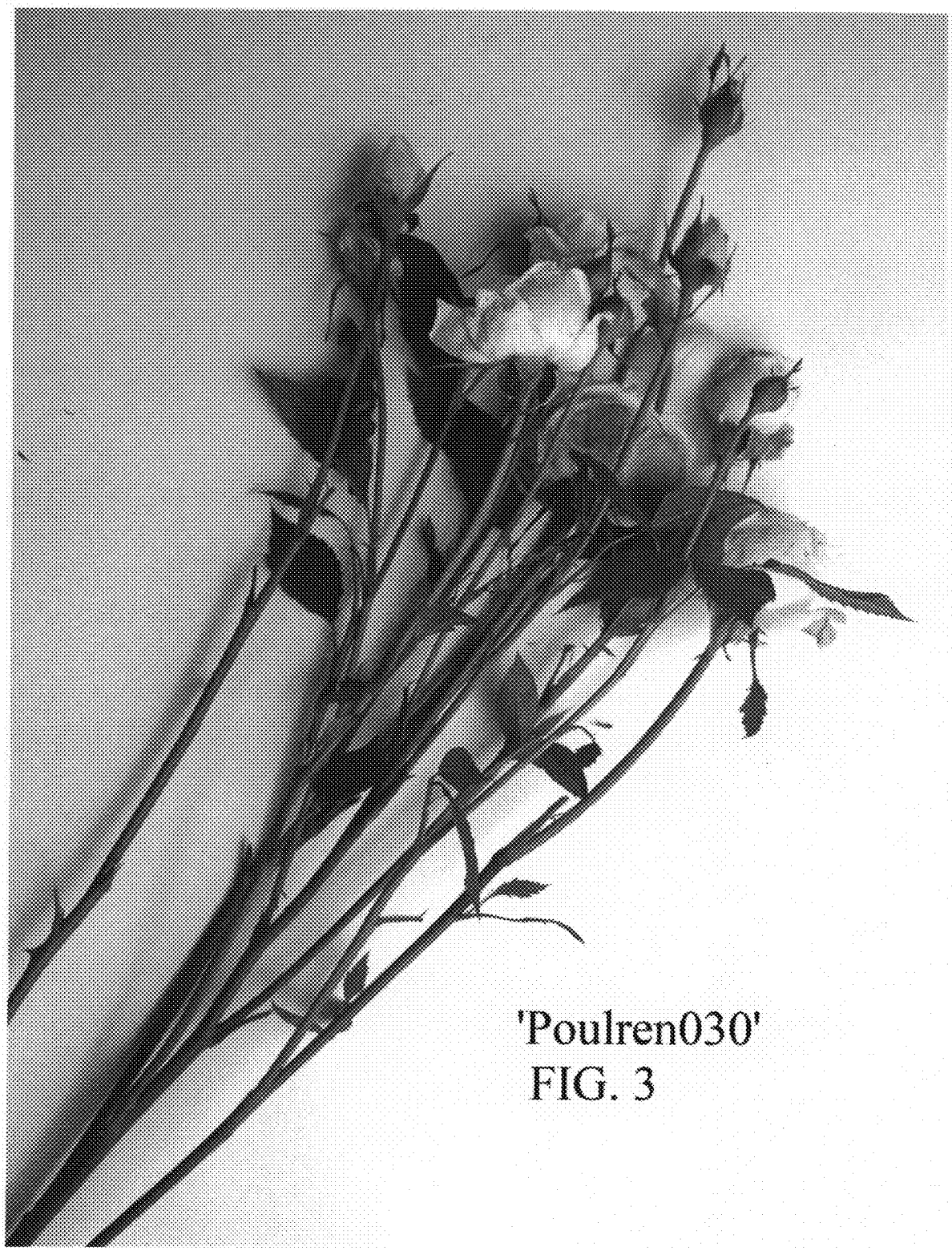

Specifically illustrated in FIG. 3 of the drawings is a cluster of open flowers on a branch. Plants shown are 2 years of age.

DETAILED DESCRIPTION OF THE VARIETY

The following is a description of 'Poulren030', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulren023', U.S. Plant Pat. No. 27,656 are compared to 'Poulren030' in Chart 1.

CHART 1

| | 'Poulren030' | 'Poulren023' |
|---|---|---|
| Petal Count | 85 | 30 |
| Flower Diameter | 65 to 75 mm | 105 mm |
| General Tonality of Flower Color | Red Group 55C with intonations of Orange-White Group 159C | Red Group 49A and Red Purple Group 62D |

FLOWER AND FLOWER BUD

Blooming habit: Continuous.

Flower bud:

*Size.*—Upon opening, 30 mm in length from base of receptacle to end of bud. Bud diameter is 15 mm.

*Bud form.*—Ovoid.

*Bud color.*—As sepals divide petals are Yellow-Green Group 144D with intonations of Red-Purple Group N57C.

*Sepal inner surface.*—Color: Yellow-Green Group 146D with intonations of Greyed-Red Group 180A. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—40 mm long, 10 mm wide.

*Receptacle.*—Texture: Smooth. Size: 5 mm in height, 10 mm wide. Color: Yellow-Green Group 144A. Shape: Campanulate.

*Pedicel.*—Surface: Smooth. Length: 80 to 90 mm. Diameter: 4 mm on average. Color: Yellow-Green Group 144A. Strength: Strong.

*Peduncle.*—Length: 10 to 35 cm. Diameter: About 5 to 6 mm. Color: Yellow-Green Group 145A with intonations of Greyed-Red Group 180A. Texture: Smooth.

Flower bud development: Flower buds are borne in clusters of about 15 to 20 flower buds per stem. Development as a panicle.

Flower bloom:

*Fragrance.*—Strong rose perfume with hints of citrus.

*Duration.*—The blooms have a duration on the plant of approximately 14 days. Petals fall cleanly away from plant after flowers have fully matured.

*Size.*—Flower diameter is 65 to 75 mm when open. Flower depth is 35 mm.

*Flower shape.*—High centered, double, with a high pointed center which is tightly closed.

*Shape of flower, side view.*—The upper and lower portions are nearly flat.

Petalage: Under normal conditions, flowers have about 85 petals, 10 of which are petaloids.

General tonality of flower: Open flowers are Red Group 55C with intonations of Orange-White Group 159C.

Petal color:

*Upon opening, outer petals.*—Upper surface: White Group N155B with intonations of Red-Purple Group 62D. At the base of the petal, Yellow Green. Lower surface: White Group N155C at the basal zone, with light intonations of Red-Purple Group 62D. At the base of the petal, Yellow Green.

*Upon opening, inner petals.*—Upper surface: At the basal zone Yellow Group 11D, mid zone Orange Group 27C, at marginal zone Red Group 38B. Lower surface: Red Group 38D with intonations of Orange-Red Group 35D. Petal spot Yellow Group 11D. After opening colors remain the same.

Petals:

*Petal reflex.*—Moderately reflexed.

*Margin.*—Entire and uniform. Moderate undulations.

*Shape.*—Broad and elliptic. Apex shape: Rounded. Base shape: Acute.

*Size.*—30 mm (l)×29 mm (w).

*Texture.*—Smooth.

*Thickness.*—Average.

Petaloids:

*Size.*—20 mm (l) by 8 mm (w).

*Quantity.*—

*Shape.*—Elliptical with an acute base and rounded and acute apex.

*Color.*—Upper side is Yellow Group 11D at the basal petaloid spot. At mid zone Orange Group 27C, at marginal zone Red Group 38B. The lower surface is Red Group 38D with intonations of Orange-Red Group 35D. A petaloid spot of Yellow Group 11D.

Reproductive flower parts:

*Pollen.*—None observed.

*Anthers.*—Size: 2 mm in length. Color: Greyed-Orange Group 163B. Quantity: 40 on average.

*Filaments.*—Color: Orange-Red Group N34A. Length: 4 mm.

*Pistils.*—Length: 8 mm. Quantity: 24 on average.

*Stigmas.*—Color: Greyed-Orange Group N170C.

*Styles.*—Color: Yellow-Green Group 144D.

*Location of stigmas.*—Level in location relative to the length of the filaments and the height of the anthers.

*Hips.*—None Observed.

PLANT

Plant growth: Upright. Plants are 80 to 120 cm in height, and 60 cm wide.

Stems:

*Color of juvenile growth.*—Yellow-Green Group 144B with intonations of Greyed-Purple Group 183B.

*Color of mature growth.*—Yellow-Green Group 144A.

*Length.*—Canes are about 55 cm from the base of the plant to the flowering portion.

*Diameter.*—About 11 mm.

*Internodes.*—On mature canes about 60 mm between nodes.

*Surface texture.*—Young wood: Smooth. Older wood: Smooth.

Long prickles:

*Incidence.*—9 prickles per 10 cm of stem.

*Size.*—Average length of prickles on mature stems is 9 mm.

*Shape.*—Upper portion is linear. Lower portion is concave.

*Color.*—Juvenile prickles: Mature prickles: Greyed-Purple Group 183B.

Plant foliage:

*Compound leaf.*—250 mm (l)×15 (w).

*Quantity.*—2 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 35 mm long, 13 mm wide. Quantity: 2 per compound leaf. Shape: Linear, slightly broad based with outward extending apices. Margins: Finely serrated. Color:

*Petiole*.—Length: About 55 mm. Diameter: 2 mm. Upper surface color: Yellow-Green Group 144A. Lower surface color: Yellow-Green Group 144A.

*Rachis*.—Length: About 70 mm. Upper surface color: Greyed-Purple Group 183A. Lower surface color: Yellow-Green Group 144A.

*Leaflet*.—Quantity: Normally 7 leaflets. Margins: Serrated. Size: Terminal leaflets are about 90 mm long, 55 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Hybrid Tea rose class named 'Poulren030', substantially as illustrated and described herein, due to its abundant pink flowers, disease resistance, and extended period of bloom.

* * * * *

'Poulren030'

'Poulren030'

'Poulren030'